United States Patent [19]
Peters et al.

[11] Patent Number: 5,550,375
[45] Date of Patent: Aug. 27, 1996

[54] INFRARED-SPECTROMETRIC SENSOR FOR GASES

[75] Inventors: Ralf-Peter Peters, Bergisch-Gladbach; Arnd Rogner, Sprockhövel; Nezih Ünal, Dortmund; Lothar Heinrich, Münster; Dierk Landwehr, Dülmen; Wolfgang A. D. Heyde, Haltern, all of Germany

[73] Assignee: microParts, Dortmund, Germany

[21] Appl. No.: 368,634

[22] Filed: Jan. 4, 1995

[30] Foreign Application Priority Data

Sep. 29, 1994 [DE] Germany ............... 44 34 814.2

[51] Int. Cl.⁶ ............................................ G01N 21/61
[52] U.S. Cl. ................................. 250/343; 356/440
[58] Field of Search ........................... 250/343, 347, 250/353; 356/440

[56] References Cited

U.S. PATENT DOCUMENTS 3,702,736  6/1971  Coggeshall ..................... 356/328
5,453,620  9/1995  Wadsworth et al. ............. 250/343

*Primary Examiner*—Davis L. Willis
*Assistant Examiner*—Richard Hanig
*Attorney, Agent, or Firm*—Oblon, Spivak, McClelland, Maier, & Neustadt, P.C.

[57] ABSTRACT

Gases can be selectively detected by the utilization of a infrared spectrometer via their specific absorption in the infrared spectral range. The sensor of the present invention is developed for continuously controlling a gaseous stream or a space filled with gas with the sensor being a single-piece shaped part manufactured as a microstructured body. The space filled with gas to be tested is between a mirror grating and entrance and exit slits for IR-radiation. The sensor is compact and robust, suitable for portable instruments, and can be manufactured at low cost and in large numbers. The sensor can also be made of metal and can be used even at an increased temperature. By using the sensor of the present invention, the safety of systems in which flammable, toxic or other gases are contained or may occur can be considerably increased in an economic manner.

17 Claims, 1 Drawing Sheet

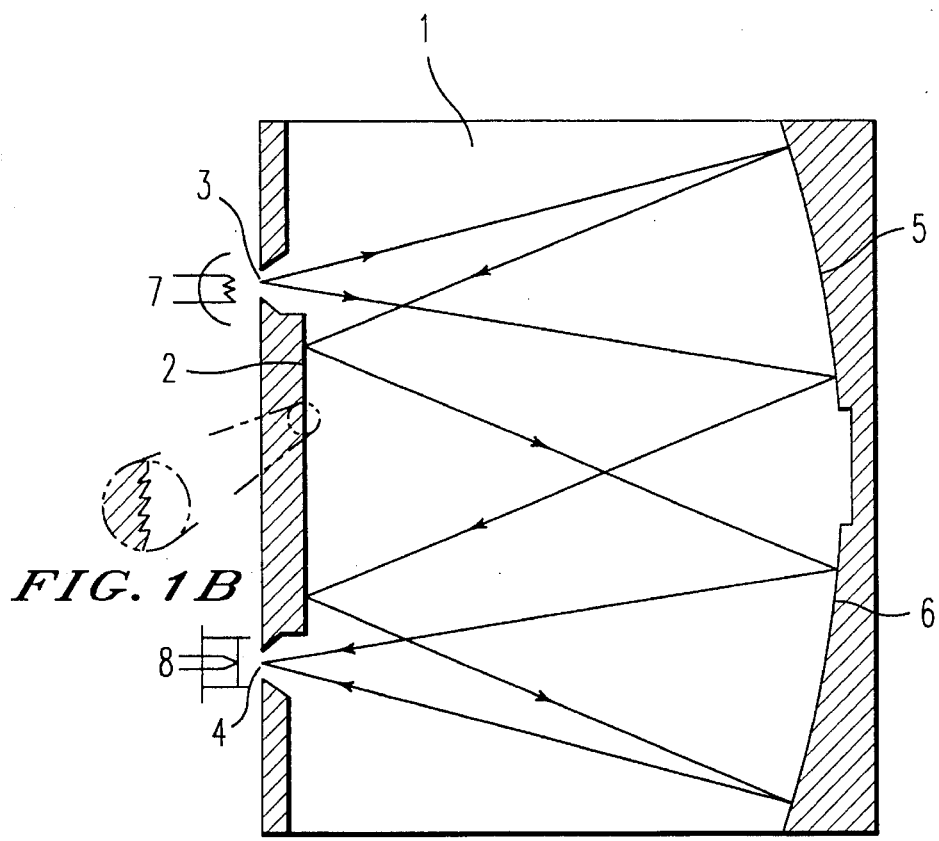
FIG. 1A
FIG. 1B
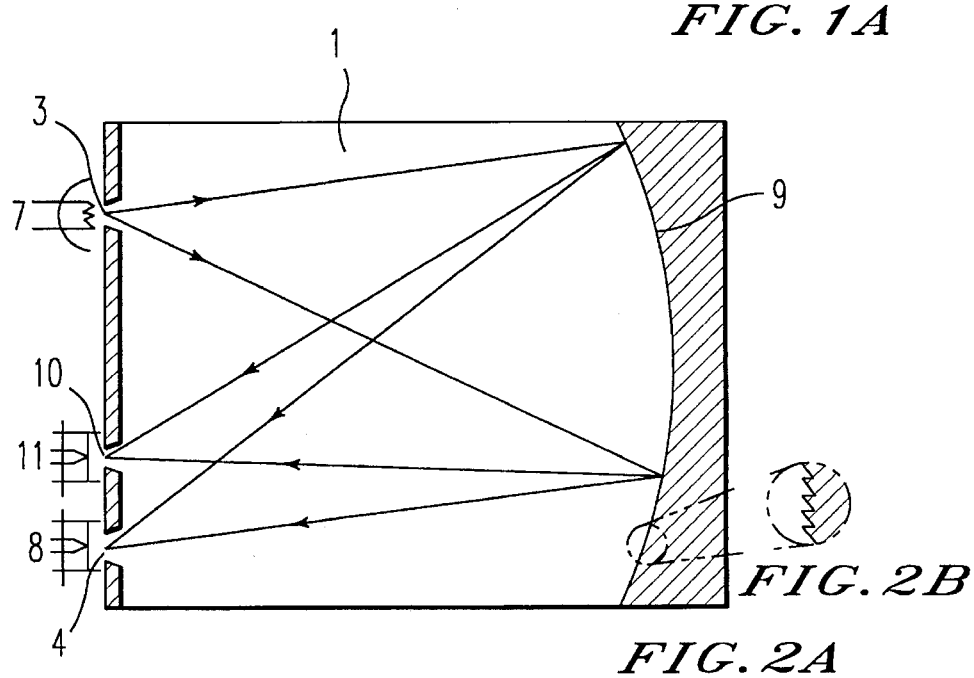
FIG. 2A
FIG. 2B
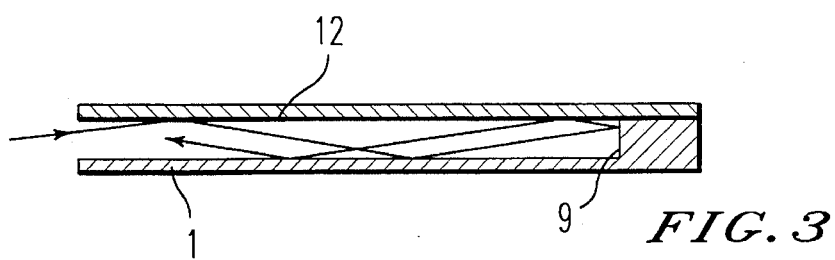
FIG. 3

1

INFRARED-SPECTROMETRIC SENSOR FOR GASES

BACKGROUND OF THE INVENTION

1. Field of the Invention

The present invention relates to a sensor for gases, by means of which the gas is detected via its absorption in an infrared (IR) spectral range. A purpose of the invention is to manufacture such a sensor economically in large numbers and with improved characteristics.

2. Discussion of the Background

In accordance with their molecular structure, gases absorb radiation in the wavelength range from a few hundreds of nanometers up to a few micrometers (corresponding to the wave number range from a few $10^4$ cm$^{-1}$ to a few $10^3$ cm$^{-1}$). On the basis of its typical absorption spectrum the gas can be identified. This forms the basis of qualitative or quantitative spectral absorption analysis of gases and gas mixtures.

Spectral absorption analysis can be carried out by known spectral instruments designed for the IR range, in which the multi-frequency radiation is dispersed by means of a prism or a transmission grating or a reflection grating. These instruments can be used to address a very wide range of complex problems and to obtain accurate results. However, the known instruments are of considerable size and they can generally be used only in a fixed position and are comparatively expensive. Tuning through a complete spectrum as a rule requires long measuring times. They demand careful treatment and handling and as a rule can be operated only by skilled personnel. Consequently, permanent monitoring, for example, of a gas mixture in terms of a given component which may occur only sporadically, by means of one of the known dispersing systems, has hitherto been restricted to special cases.

The detection of a specific gas as a rule only requires a narrow wavelength window to be filtered out, which can be achieved with the aid of an interference filter. Sensors of this type, however, can only be used to detect that particular gas. A reference wavelength for eliminating external effects cannot be used. The manufacture of narrow-band interference filters is very laborious. The characteristic curve of such filters is strongly temperature-dependent.

Oxidizable gases, e.g. natural gas, are detected with the aid of sensors in which oxygen is abstracted from a metal oxide semiconductor layer, so that the conductivity of the semiconductor layer increases. These sensors react identically to various simultaneously present oxidizable gases, i.e. they are not gas-specific. They show long-term drift and are regenerated at regular intervals by treatment with oxygen. Similar behavior is shown by pellistors, which consist of a ceramic support coated with a catalyst.

In the case of electromagnetic sensors, the gas penetrating the sensors forms ions, and as a result the sensor voltage changes. While these sensors have sufficient selectivity, they can be used only for special gases. They can be employed in a limited temperature range, and their useful life is restricted to a few years.

SUMMARY OF THE INVENTION

An object of the present invention is therefore to provide for a sensor which can be used for selective detection of gases, can be manufactured cost-effectively in large numbers and is suitable for long-term operation.

The object is achieved according to the invention by an IR-spectrometric gas sensor having the following characteristic features:

- a single-piece shaped part manufactured as a micropattern body, which comprises a base plate, a mirror grating and a connection for injecting multi-frequency IR radiation and at least one connection for extracting single-frequency IR radiation;
- a free space which contains the gas to be tested, between the mirror grating and the connections for the IR radiation;
- a cover plate above the free space, which cover plate is joined to the shaped part in a sealing manner; and
- orifices for introducing the gas into the free space and discharging it therefrom.

The mirror grating is a concave reflection grating, preferably a concave echelette grating having a matching blaze angle. Thus, the greater part of the radiation appears in a desired order of diffraction, e.g. in the first order on only one side of the grating normal. Advantageously, the mirror grating and the connection points for the IR radiation are arranged on a Rowland circle. This arrangement is self-focusing and for some applications it is sufficient or reasonable to select, instead of the Rowland circle, a curve situated in the vicinity of the circle.

The free space is covered by a plate which is joined in a sealing manner to the shaped part. The gas to be tested is introduced into, and discharged from, the space through orifices. The free space serves as a cuvette compartment for the gas to be tested.

The walls of the free space and that side of the cover plate which faces the free space is covered, if appropriate, with a metal layer having good reflectivity in the spectral range used. The space at the same time serves as a waveguide for the IR radiation.

The single-piece shaped part may contain connection elements in the form of slits, apertures and retaining structures or alignment structures for the radiation source and the radiation receiver as well as further optical elements such as planar mirrors, concave mirrors, lenses or prisms which are either integrated directly into the shaped part or are inserted into corresponding recesses in the shaped part. By means of at least one cylindrical concave mirror, the path of the IR radiation within the cuvette compartment can be extended, which is advantageous for gases having a small extinction co-efficient.

The single-piece shaped part may be composed of plastic, e.g. poly(methyl methacrylate), polysulphone, polycarbonate or of metal, e.g. nickel, nickel-cobalt, gold, copper.

The IR radiation source and the IR radiation receiver(s) may, if appropriate, be connected to the shaped part by means of an optical waveguide which guides the IR radiation. The single-piece shaped part may furthermore be fixed to a semiconductor substrate, arranged on which there are an IR radiation source, at least one IR radiation receiver and, if required, electronic elements for amplifying the detector signals and for analyzing the IR spectrum.

The gas to be tested can be introduced into the free space through one orifice and be discharged through another orifice. The connection pieces through which a e.g., pressurized gas is fed to the sensor are preferably disposed on the sensor housing. It may be expedient to leave the narrow sides of the free space entirely open, in order to permit free convection. The convection can be promoted, if the sensor has a suitable spatial arrangement, by the heat generated by the radiation source. In addition, devices may be provided which encourage convection.

In the case of dusty gases, a filter can be placed into the gas feed line. The filter may form part of the single-piece shaped part.

In order to extend the path of the IR radiation within the gas, it is possible to introduce, into the multi-frequency or the single frequency IR radiation outside the free space, a gas cuvette or a gas-filled waveguide.

Suitable radiation sources in the wavelength range from 1 µm to 10 µm (corresponding to the wave number range from $10^4$ cm$^{-1}$ to $10^3$ cm$^{-1}$) include thermal radiation sources having a wide wavelength range, such as spiral-wound filaments or thin-film radiators. Radiation sources having a narrower wavelength range include semiconductor radiation sources such as lead salt laser diodes, or radiation-emitting diodes (LED) such as InAsSbP or InGaAs diodes. Thermal radiation sources have a relatively high radiant intensity; in the case of semiconductor radiation sources, receiving the radiation may be simpler, owing to the restricted wavelength range. The radiant flux entering the spectrometer may be increased by a concave mirror behind the radiation source or by an IR-transparent convergent lens in front of the radiation source.

Suitable radiation receivers include, e.g., thermopiles, pyroelectric receivers or bolometers, as well as photoconductors and semiconductor receivers made of GaAs, PbS or PbSe. In front of the radiation receiver there may be disposed, if required, an exit slit of suitable width.

In the case of a gas sensor which is designed only for one or a few wavelengths, one or a few radiation receivers can be disposed on those points of the shaped part, at which the observed wavelengths occur. In the case of a gas sensor which is designed for covering a wide spectral range, the radiation receivers may be disposed in the form of rows.

The mode of operation of the sensor according to the invention agrees in principle with the mode of operation of the known spectrometers. In the space, in which the IR radiation is transmitted through the gas to be tested, the gas attenuates those wavelengths of the injected IR radiation, which correspond to its absorption spectrum and which are contained at smaller amplitudes in the spectrum produced by the mirror grating. The absorbed wavelengths indicate the type of the absorbing gas, the attenuation of these wavelengths being a measure for the concentration of the absorbing gas.

The single-piece shaped part is manufactured as a micro-pattern body, e.g. by X-ray lithographic etching, electroplating and casting ("LIGA" process). By means of a mask which is regionally opaque for X-rays and which is patterned in accordance with the pattern of the shaped part, a layer of an X-ray resist applied to the metal base plate is subjected to imagewise irradiation. Those areas of the resist layer which have remained soluble or have become soluble are dissolved out, followed by electodeposition of a metal in the regions dissolved out down to the base plate. The patterned resist layer is covered with metal and then separated from the metal layer patterned in a complementary manner. The patterned metal layer serves as a mold insert for casting many identical shaped parts.

The sensor according to the invention can be used for detecting various gases such as hydrocarbons, carbon monoxide, carbon dioxide, nitrogen oxides, ammonia, water vapor and others. The gases can be present in pure form, as mixtures with other gases, e.g. air, or, e.g., as the exhaust gas of a combustion plant. The sensor made of plastic can be used up to a gas temperature, up to which the plastic does not deform. The sensor made of a metal can be used at an even higher gas temperature.

The IR-spectrometric sensor for gases according to the invention has the following advantages:

The sensor has the high resolution of the grating spectrometer; it can be used to cover a plurality of narrow wavelength regions simultaneously.

The sensor has a high selectively.

The single-piece shaped part can be manufactured cost-effectively and in large numbers by means of the micropattern technology processes.

The sensor is compact, robust and accurate; it is suitable for severe conditions of use and for portable instruments. The maximum dimension of the sensor is generally less than 5 cm.

The sensor operates in the range of normal room temperature; if made of metal, it can also be used at elevated temperature.

The sensor is suitable for a multiplicity of gases. It can be used over long periods, requires little maintenance and is simple to operate.

By means of the sensor the safety of systems in which flammable, toxic or other gases are contained or may occur or may escape from such systems, can be considerably increased in an economic manner. It can be employed in the private and the commercial sector.

Accordingly, the present invention relates to an infrared spectrometric sensor for gases. The sensor comprises a single-pieced shaped part having a micro-pattern body, the shaped part comprises a base plate, a mirror grating, a connection for injecting multi-frequency IR radiation, and at least one connection for extracting single-frequency IR radiation; a free space which contains a gas to be tested, the free space being disposed between the mirror grating and the respective connections for injecting multi-frequency IR radiation and extracting single-frequency IR radiation; a cover plate above the free space, the cover plate being joined to the shape part in a sealing manner; and orifices for introducing the gas to be tested into the free space and discharging the gas therefrom.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 1A illustrates a view of the sensor of the present invention;

FIG. 1B shows an enlarged view of the planar mirror grating in FIG. 1A;

FIG. 2A illustrates a further embodiment of the inventive sensor;

FIG. 2B shows an enlarged view of the concave mirror grating in FIG. 2B; and

FIG. 3 illustrates a longitudinal section through the inventive sensor.

DESCRIPTION OF THE PREFERRED EMBODIMENTS

Referring now to the drawings, wherein like reference numerals designate identical or corresponding parts throughout the several views, FIG. 1A shows the sensor as seen from an open side of a free space. Arranged on a base plate (1) there is a planar mirror grating (2) (seen in enlarged view of FIG. 1B) and a slit (3) for injecting multi-frequency IR radiation and a slit (4) for extracting single-frequency IR radiation. Two concave mirrors (5) and (6) are situated opposite the mirror grating (2). Between the mirror grating (2) and the concave mirrors (5) and (6) there is the free space which contains the gas to be tested. The longitudinal sides of the free space are open. Arranged on the outside of the injection slit (3) there is an IR radiation source (7), and arranged on the outside of the extraction slit (4) there is an IR radiation receiver (8). In this embodiment, the essential optical elements are not situated on the Rowland circle. The parts shown hatched in FIG. 1A project above the base plate (1). The base plate (1), together with the elements (2) to (6) fixedly arranged thereon form the single-piece shaped part.

By means of the two concave mirrors (5) and (6), the IR beam is reflected within the free space, in order to extend the path of the IR through the gas.

FIG. 2A shows a further embodiment of the sensor, likewise as seen from the open end of the free space. Opposite the slits (3) and (4) a concave mirror grating (9) (seen in enlarged view of FIG. 2B) is arranged. Situated next to the slit (4) there is a slit (10) for extracting single-frequency IR radiation having a wavelength different from that at slit (4). Situated on the outside of the slit (10) there is a further radiation receiver (11). By means of one of the two radiation receivers (8) and (11), a wavelength is received which is absorbed by the gas. By means of the other radiation receiver, a reference wavelength is received which is not absorbed by the gas.

FIG. 3 shows a longitudinal section through the sensor. The free space is covered by a cover plate (12). The radiation coming from the IR radiation source undergoes multiple reflection on the walls of the free space.

EXAMPLE 1

IR-spectrometric Sensor for Flammable Gases

Flammable hydrocarbons such as methane, ethane, propane an butane absorb IR radiation in the range around 3.38 µm (2960 cm$^{-1}$). The detection of methane in air makes use of an IR-spectrometric sensor according to the invention.

The sensor according to FIG. 2A is approximately 25 mm long and approximately 20 mm wide. The free space has a height of approximately 500 µm. The inside of the single-piece shaped part fabricated by means of the LIGA technique and made of poly(methyl methacrylate) and the inside of the cover plate made of poly(methyl methacrylate) are gold-plated, as is the mirror grating. The mirror grating has 200 lines/mm; the blaze angle is matched to the maximum reflection of the mirror grating in the range 3.3 µm (3030 cm$^{-1}$) in the first order of diffraction.

The spectrometer entrance slit (3), which has a width of approximately 0.4 mm, is illuminated with a narrow-band pulsed IR LED which is made of InGaAs and whose maximum radiant intensity is at 3.4 µm (2940 cm$^{-1}$) with a half-intensity width of approximately 0.4 µm (approximately 350 cm$^{-1}$). The radiation reflected by grating is directed onto the two slits (4), (10) having widths of approximately 0.4 mm; one slit is situated at the position at which the wavelength 3.3 µm (3030 cm$^{-1}$) appears, the other at the point at which the wavelength 2.78 µm (3600 cm$^{-1}$) appears. This wavelength is not appreciably absorbed either by methane or by air. Disposed behind each exit slit (4), (10) there is a lead selenide radiation receiver.

The entrance slit, the two exit slits and the center of the mirror grating are situated on a Rowland circle having a radius of 11 mm. The radius of curvature of the mirror grating is 22 mm.

The wavelength 3.3 µm (3030 cm$^{-1}$) is the measuring wavelength, the wavelength 2.78 µm (3600 cm$^{-1}$) is the reference wavelength. By means of the reference wavelength, sources of interference such as temperature fluctuations or short-term and long-term changes in the radiant intensity of the IR LED are detected and taken into account in the evaluation of the intensity of the output signal.

The sensor's free space, which is used as a gas cuvette, has pressurized gas flowing through it with a flow rate of approximately 10 cm$^3$/h. The gas essentially consists of air and may at times contain methane.

As soon as the gas contains methane, the intensity received by the radiation receiver at 3.38 µm (2960 cm$^{-1}$) diminishes in accordance with the extinction law as the concentration of methane increases.

This sensor can be used to detect methane percentages in air, which amount to approximately 10% of the concentration of the methane containing ignitable mixture, i.e. approximately 5% methane in air, quasi-continuously. This makes it possible to detect leaks in gas-operated plants.

EXAMPLE 2

IR-spectrometric Sensor for the Exhaust Gas of a Combustion Plant

The exhaust gas of a combustion plant, in addition to nitrogen, oxygen, carbon dioxide and water vapor, also contains carbon monoxide, unburned hydrocarbons and nitrogen oxides. A cold branch stream of the exhaust gas is passed to a sensor according to the invention and is analyzed quasi-continuously.

The sensor is constructed in a manner similar to the sensor used in Example 1. The IR radiation source used, with a wide spectral range, is a thermal radiator (NiCr wire). Part of the exhaust gas passed into the free space flows past the IR radiation source. As a result, the radiation source is cooled and the flow of the exhaust gas through the free space is encouraged. The sensor, however, contains an exit slit, approximately 8 mm wide, at that point of the Rowland circle, at which the wavelength range from 2.5 µm to 7.7 µm (from 4000 cm$^{-1}$ to 1300 cm$^{-1}$) appears. Behind the exit slit, 64 thermopiles are arranged next to one another which each have a width of 120 µm and a height of approximately 1 mm. The effective area of each thermopile has a width of 100 µm and a height of 400 µm. These radiation receivers arranged in a row-like manner are used to measure simultaneously the intensity of bands, each having a width of approximately 80 nm, of the wavelength range applied to the receiver row. On the basis of the distribution of the intensity of the 64 signals, the proportions of the gases carbon monoxide, hydrocarbons and nitrogen oxides contained in the exhaust gas are determined quasi-continuously. Once the concentration of these gases in the exhaust gas are known, the mode of operation of the combustion plant is optimized.

EXAMPLE 3

IR-spectrometer Sensor with Integrated Ancillary Parts

The sensor contains the single-piece shaped part according to FIG. 2A. On the outside of the entrance and exit slits, the shaped part contains a cavity having coated walls for radiation conversion within the wavelength range under consideration.

The cover plate (12) for the free space consists of a silicon plate which contains a thin-film resistance heater element for generating the IR radiation, as well as a plurality of thermopiles as radiation receivers. The cover plate (12) further contains a plurality of preamplifiers for amplifying the signals of the radiation receiver and an electronic circuit for analyzing and processing the signals, as well as electronic elements for driving the IR radiation source. Radiation source and radiation receiver are arranged at those points of the cover plate, which, when the plate is placed on the single piece shaped part, are situated above the cavities in front of the entrance and exit slits.

The radiation entering from above into the cavity in front of the entrance slit is absorbed by the walls of the cavity, is radiated isotropically and through the entrance slit enters the free space of the spectrometer. The radiation is thus deviated by 90°.

The radiation which enters through the exit slit into the cavity in front of the exit slit and is reflected by the mirror grating is absorbed by the walls of the cavity, is radiated isotropically and impinges on the radiation receiver.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. An infrared sensor for gases, the sensor comprising:
    a single-piece shaped part having a micropattern body, the shaped part comprising a base plate, a mirror grating, a connection for injecting multi-frequency IR radiation, and at least one connection for extracting single-frequency IR radiation;
    a free space which contains a gas to be tested, the free space being disposed between the mirror grating and the respective connections for injecting multi-frequency IR radiation and extracting single frequency IR radiation;
    a cover plate above the free space, said cover plate being joined to the shaped part in a sealing manner so as to cover the free space; and
    orifices for introducing the gas to be tested into the free space and discharging the gas therefrom.

2. A sensor according to claim 1, wherein the mirror grating is a concave reflection grating.

3. A sensor according to claim 1, wherein the mirror grating is a concave echelette grating having a matching blaze angle.

4. A sensor according to claim 1, wherein the mirror grating and the connections for the IR radiation are arranged on a Rowland circle or on a curve which is situated in a vicinity of a Rowland circle.

5. A sensor according to claim 4, wherein a side of the cover plate which faces the free space is covered with a metallic layer which reflects the IR radiation.

6. A sensor according to claim 1, wherein said connections for the IR radiation comprise slits, and wherein a radiation source is positioned outside said connection for injecting multi-frequency IR radiation, and at least one radiation receiver is positioned outside said at least one connection for extracting single-frequency IR radiation.

7. A sensor according to claim 1, further comprising:
    an optical element which is positioned opposite the mirror grating and is either integrated directly into the shaped part or is inserted into corresponding recesses in the shaped part.

8. A sensor according to claim 7, wherein said optical element is a concave mirror, lens or prism.

9. A sensor according to claim 7, wherein said optical element is at least one cylindrical concave mirror which is integrated into the shaped part and permits a path of the IR radiation within the free space to be extended.

10. A sensor according to claim 1, wherein said single-piece shaped part is composed of plastic or of metal.

11. A sensor according to claim 10, wherein said plastic of said single-piece shaped part is one of poly (methyl methacrylate), polysulphone or polycarbonate, and said metal of said single-piece shaped part is one of nickel, nickel-cobalt, gold or copper.

12. A sensor according to claim 6, wherein an optical waveguide guides the IR radiation and permits the IR radiation source to be connected to the shaped part.

13. A sensor according to claim 6, wherein at least one optical waveguide guides the IR radiation and permits IR radiation receivers to be connected to the shaped part.

14. A sensor according to claim 1, wherein said single-piece shaped part is fixed to a semiconductor substrate, and an IR radiation source and at least one IR radiation receiver are positioned adjacent to said connections for the IR radiation.

15. A sensor according to claim 1, wherein said gas to be tested is gaseous hydrocarbons such as methane, ethane, propane or butane, or carbon dioxide, carbon monoxide, nitrogen oxide, water vapor, ammonia, in a gas mixture.

16. A sensor according to claim 1, wherein a testing of said gas to be tested comprises a quantitative analysis of gases or gas mixtures.

17. A sensor according to claim 1, wherein said free space defines a gas chamber.

\* \* \* \* \*